United States Patent [19]
Grünenfelder et al.

[11] Patent Number: 5,997,293
[45] Date of Patent: Dec. 7, 1999

[54] FURNACE FOR FIRING DENTAL CERAMIC MATERIAL

[75] Inventors: Robert Grünenfelder; Andreas Meier; Jürgen Seger, all of Vaduz, Liechtenstein

[73] Assignee: Ivoclar AG, Schaan, Liechtenstein

[21] Appl. No.: 09/073,531

[22] Filed: May 6, 1998

[30] Foreign Application Priority Data

Jun. 18, 1997 [DE] Germany .......................... 197 25 866

[51] Int. Cl.$^6$ .................................................. B25J 11/00
[52] U.S. Cl. .................................................. 432/206; 901/6
[58] Field of Search ................................. 432/206, 208, 432/239; 414/222, 225; 901/6

[56] References Cited

U.S. PATENT DOCUMENTS

| 4,300,037 | 11/1981 | Padden . | |
|---|---|---|---|
| 4,828,490 | 5/1989 | Indig | 432/241 |
| 5,445,491 | 8/1995 | Nakagawa et al. | 414/222 |
| 5,651,823 | 7/1997 | Parodi et al. | 414/225 |
| 5,759,006 | 6/1998 | Miyamoto et al. | 414/222 |
| 5,788,485 | 8/1998 | Grunenfelder et al. | 432/206 |

FOREIGN PATENT DOCUMENTS

| 26 32 846 | 2/1977 | Germany . |
| 32 31 546 | 3/1984 | Germany . |
| 37 19 536 | 12/1987 | Germany . |
| 94 09 205 | 7/1994 | Germany . |
| 195 42 984 | 12/1996 | Germany . |
| 2 191 568 | 12/1987 | United Kingdom . |
| 2 201 495 | 9/1988 | United Kingdom . |

*Primary Examiner*—Teresa Walberg
*Assistant Examiner*—Gregory A. Wilson
*Attorney, Agent, or Firm*—John C. Thompson; Alan S. Korman

[57] ABSTRACT

The furnace for firing ceramic materials has a working surface including a firing area and a storage area. A hood is provided which is moveable motorically relative to the working surface and positioned above the firing area to define the firing chamber. A robot arm for moving the ceramic material into and out of the firing area is provided.

12 Claims, 3 Drawing Sheets

FURNACE FOR FIRING DENTAL CERAMIC MATERIAL

The present invention relates to a furnace comprising a working surface for storing the ceramic material, especially a dental material, to be fired and further comprising a furnace hood moveable relative to the working surface.

Such a furnace is, for example, known from German Patent 195 42 984 but also from German Patent 26 32 846. These furnaces have been successful in practice and are successfully sold by the applicant.

From German Patent 37 19 536 a furnace is known in which the support for the material to be fired is pivotable by horizontal arms. This technical solution is relatively complicated and requires at least two support plates for the ceramic material including the corresponding electro-mechanical controls whereby additionally it must be ensured that the support plates will not collide with one another. The furnace chamber is relatively large in order to accommodate the heat-resistant arms. The pre-heating period in relation to the energy output, is relatively long so that it is not surprising that this solution has not found acceptance in practice.

An important aspect for the quality of dental ceramics is the precise compliance with the firing curve designed for the receptive dental ceramic. This includes the resting time which, as is known per se, must be adhered to during the cooling period. During the resting time, jarring, etc. must be avoided in order to ensure solidification of the ceramic material and especially in order to prevent tension cracks.

It therefore has been suggested to make the working surface of the furnace having a furnace hood as smooth as possible in order to ensure that the material to be fired, after completion of firing, can be moved across the surface without jarring and can be positioned in the resting position to observe the resting period while the next dental ceramic material is already supplied, for the next firing step. According to the first mentioned patent document, to both sides of the area of the furnace hood, i.e., to both sides of the firing area, storage surfaces are provided. This design allows to guide the material to be fired from the storage surface on one side unto the furnace area and to cool or harden the already fired ceramic on the storage surface at the other side.

The smooth working surface, however, does not provide stops for an exact positioning of the material to be fired or of the fired ceramic. Therefore, it has been suggested to provide heat-resistant markings on the working surface which allow a precise positioning of the goods to be fires within the firing area. However, since in practice in a dental laboratory a fast and precise working is required, it may occur that the markings cannot be observed precisely, especially when differently dimensioned support plates for the materials to be fired are used, depending on the different types of dental ceramics to be fired.

Thus, it has been suggested, to center by a type of insertion slot the furnace hood, the dental ceramic, or its support plate. An exact sintering is important in order to ensure a uniform temperature loading of the material to be fired during centering and thus to avoid tension cracks during the firing process. Such special stops, however, require a special embodiment of the furnace hood which, in order to accommodate the respective slanted portions, must be larger than conventional hoods. Due to the usually one-sided contact between the support plate and the furnace hood, there is a tendency for one-sided heating. In general, it is desirable to avoid contact between the material to be fired and the furnace hood.

It is therefore an object of the present invention to provide a furnace of the aforementioned kind with which a tension crack-free, or at least tension crack-reduced, manufacture of dental ceramic materials can be ensured even when increased output is demanded.

SUMMARY OF THE INVENTION

A furnace for firing ceramic material according to the present invention is primarily characterized by:
   A working surface having a firing area and a storage area:
      The hood moveable motorically relative to the working surface and positioned above the firing area to define a firing chamber;
   A robot arm for moving the ceramic material into and out of the firing area.

Advantageously, the furnace comprises a program control controlling movement of the robot arm and of the hood such that the hood is lowered onto the firing area when the robot arm is not within the firing area.

Preferably, the robot arm is a pivot arm connected to the working surface.

The furnace may comprise a support plate for the ceramic material, wherein the robot arm is rotatable and liftable for moving the ceramic material above the support plate and pivoting the ceramic material relative to the support plate.

The working surface is preferably planar from the firing area to the storage area.

Advantageously, the furnace further comprises a support plate for the ceramic material, wherein the support plate is detachably connected to the robot arm by frictional and/or positive locking connection.

Preferably, the support plate for the ceramic material is moveably supported on the working surface and moved on the working surface by the robot arm. The support plate is preferably comprised of heat-resistant material and has securing elements. The robot arm comprises gripping elements for receiving the securing elements. The gripping elements include a catch area for safely connecting the gripping elements and the securing elements when the actual position of the ceramic material in the firing area or in the storage area deviates from a desired position.

The robot arm may also be moveable in a transverse direction.

The program control preferably includes a control function for selecting the firing curve of the ceramic material.

The robot arm is advantageously moveable into a plurality of storage positions in the storage area.

The inventive furnace is characterized by realizing a robot arm for supplying and removing the material to be fired or the fired ceramic material into and out of the firing area. A robot arm may in the context of the present invention refer to any suitable operating device or manipulating device that allows moving the goods to be fired or the already fired ceramic between the firing area and the storage area and vise versa. The invention provides surprisingly for the manufacture of tension crack-reduced dental ceramics. This is due to the fact that the resting time can be maintained within the required range, since the inventive furnace allows for the first time continuous operation through the night, so that the resting times can be prolonged even though the output is increased.

Due to the operation of the device with the aid of the robot arm it is possible to ensure always the same and exact positioning of the material to be fired in the center of the firing area, and the operator can no longer cause a one-sided heating and thus the formation of tension cracks during the firing process by accidently performing operating errors.

Inventively, this is ensured by the motorically controlled pivoting of the robot arm together with the goods to be fired into the firing area. The cooperation of the securing elements at the support plate with the gripping elements at the robot arm makes it possible to maintain the support plate, after loosening the connection to the robot arm, exactly in the desired position so that the firing process can be realized with uniform quality.

The robot arm can be embodied in any suitable and desired manner. Preferably, it is supported on a pivot axis and is adjustable at least in the are of its gripping elements with respect to its height. Even for such a two-dimensionally adjustable embodiment feeding and removal of the material to be fired or of the fired ceramic material into and out of the firing area is possible.

After placing the prepared material to be fired onto the storage area, the robot arm is programed-controlled such that it is lowered, so that its gripping elements come into contact with the securing elements of the support plate. In the lowered position the support plate is pivoted across the complete by planar working surface to the desired firing position in the firing In this position the robot arm is lifted again so that its gripping elements will become detached from the securing elements. The robot arm is then pivoted back then into its initial position, and the lifted and open furnace hood is lowered onto the firing area in order to begin the firing process. After completion of firing, the hood is lifted and pivoted, and the robot arm is returned into the firing area where, after being lowered, it grips with its gripping elements again the securing elements of the support plate and returns the fired goods on the support plate into the storage position.

It is preferred that the securing elements are provided so as to be universally attachable and securable to the gripping elements. Inventively, it especially favorable that different types of support plates can be used whereby coupling between the gripping elements and the securing elements ensures a defined centered position.

It is preferred to realize the pivoting action of the goods to be fired very slowly, whereby a slow acceleration and breaking action of the pivot movement is realizable.

The simple embodiment of the inventive furnace allows a tension crack-free processing and night operation. The invention allows furthermore the possibility to realize assembly line type operation for firing multiple dental ceramics during the night. For this purpose it is possible to realize via the robot arm a lifting and lowering of the support plate whereby the dental ceramics positioned adjacent to one another on their support plates are separately supplied to, fired in, and removed from the firing area.

According to an alternative embodiment, the supply and removal area are separated from one another, for example, by being arranged to the right and left, neighboring the firing area. The robot arm can be supported at a pivot axis preferably in the rearward area of the furnace hood, whereby it is understood that a certain spacing must be ensured for the lifting mechanism of the furnace hood.

It is understood that the inventive furnace may be provided with a lifting mechanism, a pivot mechanism as well as a combination thereof with which the furnace hood is first lifted and then pivoted whereby in all embodiments the robot arm is supported such that it will not collide with the lifting or pivot mechanism.

According to another embodiment it is suggested that the robot arm performs a three-dimensional movement and operation. This embodiment allows a very exact placing of the material to be fired when the working surface is not entirely planar and the firing area is slightly raised relative to the surrounding area.

The realization of the griping elements and of the securing elements can be adjusted in wide ranges to the specific requirements. For example, it is possible to have the securing elements provided at the support plate perform gripping functions instead of the gripping elements at the robot arm so that the gripping elements of the robot arm act as securing elements.

Even though a motion control can be realized presently with a precision of 1 mm, it is preferred to provide at the gripping elements a small insertion slant in order to provide a catch area at the robot arm of approximately 5–10 mm. This is less important in context with coupling within the firing area, since, in general, no positional changes of the support plate will occur in this area, with the exception of thermal expansion that is within a range of sub mm. It is instead preferred to provide a catch area so that within the storage area the dental ceramic material, placed there by a technician, can be gripped safely.

While the simplest embodiment of the inventive gripping and securing elements is limited to a purely mechanical locking action, it is also possible to lock the gripping elements and securing elements selectively mechanically or electromagnetically. This solution is preferred when a lifting of the support plate must be realized.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be explained with the aid of several specific embodiments utilizing FIGS. 1–3.

Figure 1:
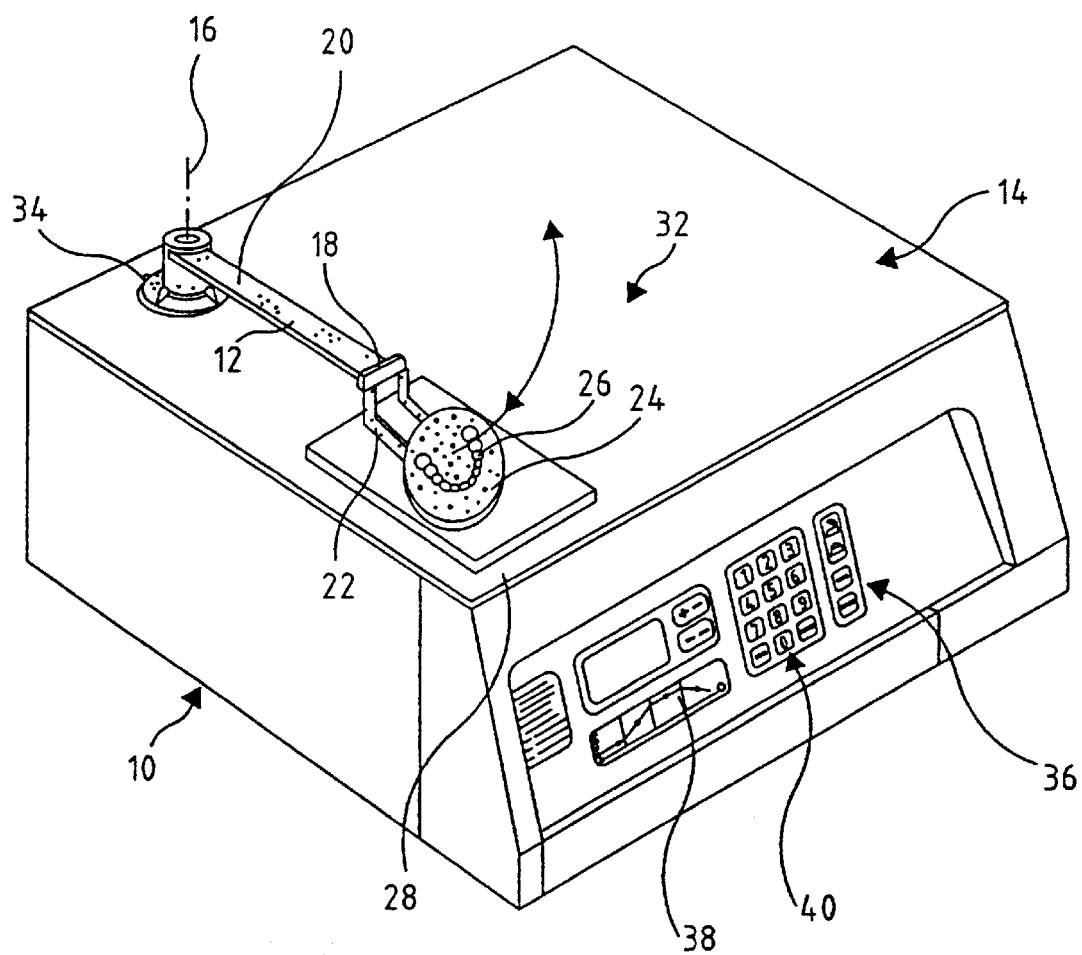
FIG. 1 is a schematic view of the inventive furnace in a perspective illustration of a first embodiment whereby the hood has been eliminated in order to facilitate understanding of the drawings.

The furnace 10 represented in FIG. 1 comprises a robot arm 12 which is supported at the working surface 14.

It is understood that instead of the disclosed support of the robot arm 12 at the working surface 14, the robot arm 12 can also be supported at any other suitable position at the furnace. The robot arm is pivotable about vertical pivot axis 16 and is height-adjustable along the pivot axis 16. It comprises gripping elements 18 at its front end 20 which are designed such that they grip the securing elements 22 of support plate 24 which receives as the material to be fired a dental ceramic 26

The drawings show schematically a denture as the dental ceramic to be fired whereby it is understood that, instead, any suitable or desired dental ceramic or any other suitable material for firing can be used.

Even though the support plate 24 in the shown Figures is of a rectangular shape, it is understood that any suitable, for example, round shape can also be realized, provided that the dental ceramic materials to be fired can be safely supported on the support plate 24. The dimensions of the support plate are to be selected such that the support plate 24 fits into the interior of the hood 30 shown in FIG. 2.

In the representation according to FIG. 1 the robot arm 12 as well as the support plate 24 and thus the material to be fired 26 are located within the storage area 28, i.e., external to the hood 30. By pivoting the robot arm 12 a movement into the firing area 32 is possible which can be covered by the hood 30 shown in FIG. 2. For this purpose, the gripping elements 18 grip the securing elements 22 and perform a pivoting action about substantially 45°.

For detaching the gripping elements 18 from the securing elements 22, it is suggested that the robot arm 12 is lifted, whereby in the shown embodiment the lifting takes places in the direction of the pivot axis 16. Instead, it is possible to provide a further horizontal pivot axis in the area of the support 34 of the robot arm so that the robot arm 12 for the lifting action can be pivoted upwardly.

According to a further modified embodiment it is suggested to provide solenoids at the gripping elements which are acting on a ferromagnetic area of the securing elements. This solution allows to lift selectively the securing element and thus the support plate 24 when the gripping element 18 is lifted.

In the represented embodiment the securing elements 22 are comprised of two upwardly projecting bearing pins which are designed for engaging respective bushing recesses in the gripping elements 18. It is understood that any suitable other detachable connection can be inventively realized.

An important feature of the inventive solution is the realization of a program control 36 which controls the motoric actuation of the robot arm 12 as well as the hood 30 and also the schematically represented firing curve 38.

The storage area 28 and the firing area 32, in a modified embodiment, can be provided with sensors which support the action of the program control and which thus prevent erroneous operations. The respective sensors can ensure that the robot arm 12 securely grips the support plate 24 in order to avoid faulty firing of the material and realizes correct positioning.

As can be seen in the Figures, a plurality of keys can be provided within the operating panel 40 for adjusting the firing curve as well as a key 42 for realizing a "hood open" position and a key 44 for realizing a "hood closed" position. In connection with respective sensors, the key "hood open" can also result in movement of the support plate from the storage area into the firing area, and activation of the key 44 "hood closed" the robot arm 12 can be detached from the support plate 24 and returned into the storage area in order to start the firing process.

When, on the other hand, the key 42 is actuated during the firing process, for example, in order to interrupt an accidentally started firing operation, the hood 30 is lifted, the robot arm 12 is pivoted into the firing area 32, grips the support plate 24, and pivots it into the storage area 28. When no support plate 24 is within the storage area 28 and the key 44 is pressed, no loading of a support plate will be performed due to sensor control, but instead the hood 30 is lowered.

Figure 2:
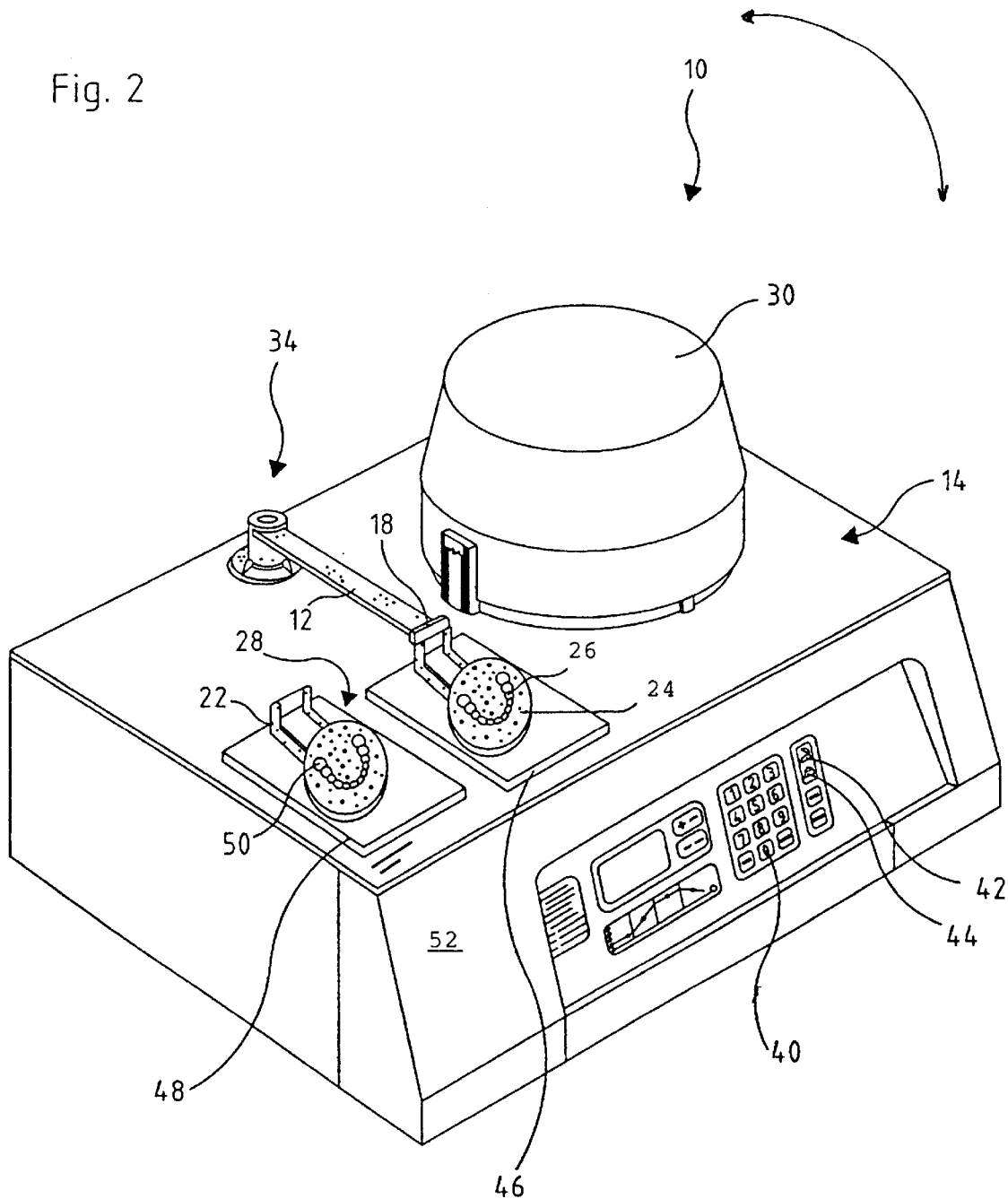
FIG. 2 is a perspective representation of a further embodiment of the inventive furnace.

The embodiment accord to FIG. 2 is characterized by schematically represented automatic loading of the firing chamber with the plurality of dental ceramics to be fired. It is understood that it is preferred to fire similar dental ceramic materials 26, whereby, however, it is possible to select via the operating panel 40 for each dental ceramic a special firing curve.

In the embodiment according to FIG. 2, the support plate 24 to the right with unfired material 26 is moved, after lifting of the hood 30 into the firing area 32 and is then fired. After completion of the actual firing process, the support plate 24 is returned into the same initial position 46 of the storage area 28 and is placed therefor undergoing the resting period.

During this time the second support plate 48 with the second material to be fired 50 can be gripped by gripping element 18 of the robot arm 12 and secured thereat by its securing elements 22. In this embodiment the design of the securing elements 22 and gripping elements 18 is such that lifting of the support plates 24 and 48 is possible.

The second support plate 48 is lifted and moved across the first support plate 24 into the firing area 32. After competition of firing of the second material to be fired 50, the support plate 48 is removed in the same manner from the firing area 32 is then returned via the first position 46 of the storage area 28 into the second position 52 in which it can undergo the resting period.

In the meantime, the resting period for the dental ceramic 26 positioned in the first position 46 has elapsed. A third dental ceramic can then be placed on a respective support plate into this position and can be moved into the firing area 32 where it is to be fired.

In this manner, the embodiment according to FIG. 2 allows for a continuous operation and increase of the output despite the fact that the required resting period is observed.

It is understood that it is favorable to increase the number of positions within the storage area 28, i.e., to have more than the first position 46 and the second position 52. This embodiment allows for a continuous operation in which the furnace is, for example, loaded at night with ten dental ceramic materials which are finish-fired the next morning whereby it is understood that in this embodiment it is also possible to program the desired firing curve for each dental ceramic material.

While in the embodiment according to FIG. 2 the storage area is designed to be only to the left of the hood 30 and the robot arm 12 with its support 34 is in the rearward area of hood 30 to the left, it is possible according to another alternative, not represented in the drawings, to provide a supply or loading area for dental ceramics to the left of the hood 30 and to provide a removal area to the right of the hood 30. In this embodiment, it may be advantageous when the robot arm 12 is supported either centrally behind the hood 30 or provided with a telescopic arm, in order to reach the positions at the far side of the two part storage area 28.

Figure 3:
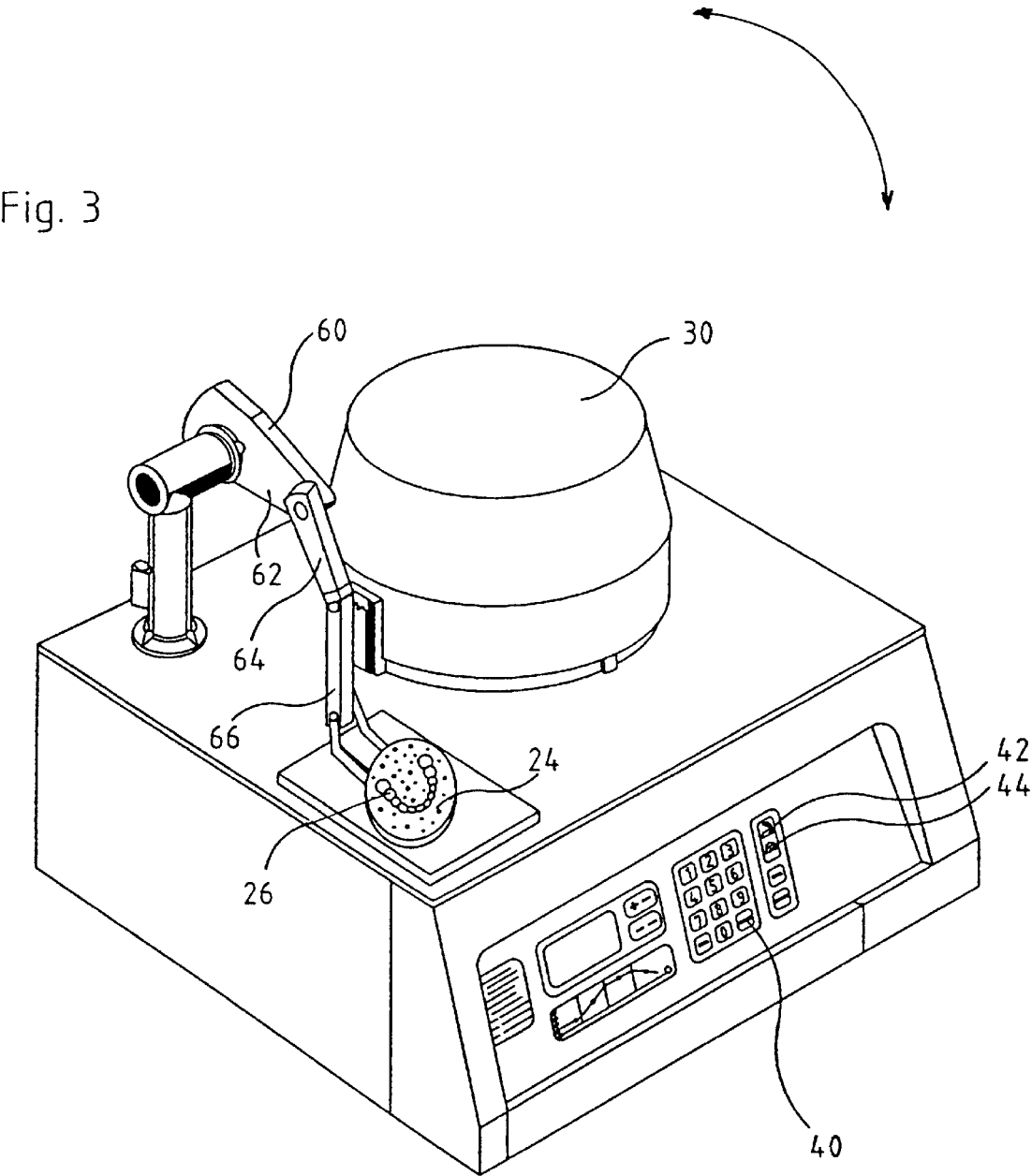
FIG. 3 a perspective representation of a third embodiment of the inventive furnace.

A modified embodiment of the inventive furnace is shown in FIG. 3. This embodiment corresponds substantially to the simple embodiment according to FIG. 1, whereby instead of the robot arm 12 a type of robot arm 60 is provided which comprises multiple pivotable members 62, 64, and 66 allowing a multi-dimensional movement of the support plate 24.

The present invention is, of course, in no way restricted to the specific disclosure of the specification and drawings, but also encompasses any modifications within the scope of the appended claims.

What is claimed is:

1. A furnace for firing ceramic material, said furnace comprising:
   a working station having a firing area and a storage area;
   a hood moveable between hood open and hood closed positions relative to said working surface and positioned above said firing area to define a firing chamber; and;
   a robot arm for moving the ceramic material into and out of said firing area.

2. A furnace according to claim 1, comprising a program control controlling movement of said robot arm and of said hood such that said hood is lowered onto said firing area when said robot arm is not within said firing area.

3. A furnace according to claim 2, wherein said program control 40 includes a control function for selecting a firing curve of the ceramic material.

4. A furnace according to claim 1, wherein said robot arm is a pivot arm connected to said working surface.

5. A furnace according to claim 1, comprising a support plate for the ceramic material, wherein said robot arm is rotatable and liftable for moving the ceramic material above said support plate and pivoting the ceramic material relative to said support plate.

6. A furnace according to claim 1, wherein said working surface is planar from said firing area to said storage area.

7. A furnace according to claim 1, further comprising a support plate for the ceramic material, wherein said support plate is detachably connected to said robot arm by frictional or positive locking connection.

8. A furnace according to claim 1, further comprising a support plate for the ceramic material, wherein said support plate is detachably connected to said robot arm by frictional and positive locking connection.

9. A furnace according to claim 1, further comprising a support plate for the ceramic material, wherein said support plate is moveably supported on said working surface and moved on said working surface by said robot arm.

10. A furnace according to claim 1, further comprising a support plate for the ceramic material, wherein:

said support plate consists of heat-resistant material and comprises securing elements;

said robot arm comprises gripping elements for receiving said securing elements;

said gripping elements comprising a catch area for safely connecting said gripping elements and said securing elements when an actual position of the ceramic material in said firing area or in said storage area deviates from a desired position.

11. A furnace according to claim 1, wherein said robot arm is moveable in a transverse direction.

12. A furnace according to claim 1, wherein said robot arm is moveable into a plurality of storage positions in said storage area.

* * * * *

UNITED STATES PATENT AND TRADEMARK OFFICE
CERTIFICATE OF CORRECTION

PATENT NO. : 5,997,293
DATED : December 7, 1999
INVENTOR(S) : Robert Grunenfelder et al It is certified that error appears in the above-indentified patent and that said Letters Patent is hereby corrected as shown below:

In claim 1, line 3, change "station" to --surface--.

Signed and Sealed this

Fifth Day of September, 2000

Attest:

Q. TODD DICKINSON

Attesting Officer

Director of Patents and Trademarks